United States Patent
Li et al.

(10) Patent No.: US 11,227,700 B2
(45) Date of Patent: Jan. 18, 2022

(54) METHOD AND APPARATUS OF CORRECTING COLLIMATOR OF RADIOTHERAPY EQUIPMENT

(71) Applicants: OUR UNITED CORPORATION, Shaanxi (CN); SHENZHEN OUR NEW MEDICAL TECHNOLOGIES DEVELOPMENT CO., LTD., Shenzhen (CN)

(72) Inventors: Jiuliang Li, Shaanxi (CN); Hao Yan, Shaanxi (CN); Jinsheng Li, Shaanxi (CN); Tianchang Gou, Shaanxi (CN); Chun Luo, Shaanxi (CN)

(73) Assignees: OUR UNITED CORPORATION; SHENZHEN OUR NEW MEDICAL TECHNOLOGIES DEVELOPMENT CO., LTD.

( * ) Notice: Subject to any disclaimer, the term of this patent is extended or adjusted under 35 U.S.C. 154(b) by 0 days.

(21) Appl. No.: 17/005,699

(22) Filed: Aug. 28, 2020

(65) Prior Publication Data

US 2020/0395142 A1 Dec. 17, 2020

Related U.S. Application Data

(63) Continuation-in-part of application No. PCT/CN2018/099483, filed on Aug. 8, 2018.

(51) Int. Cl.
*A61N 5/10* (2006.01)
*G21K 1/02* (2006.01)
*A61B 6/06* (2006.01)

(52) U.S. Cl.
CPC ............. *G21K 1/025* (2013.01); *A61B 6/06* (2013.01); *A61N 5/1045* (2013.01); *A61N 5/1084* (2013.01)

(58) Field of Classification Search
CPC ............. A61N 5/1081; A61N 5/1045; A61N 2005/005; A61N 2005/1094;
(Continued)

(56) References Cited

U.S. PATENT DOCUMENTS

2008/0253516 A1  10/2008  Hui et al. ................... 378/62
2010/0329413 A1  12/2010  Zhou et al. ................. 378/4
(Continued)

FOREIGN PATENT DOCUMENTS

CN      1919373 A    2/2007
CN    101927065 A   12/2010
(Continued)

OTHER PUBLICATIONS

International Search Report dated May 9, 2019 in corresponding PCT International Application No. PCT/CN2018/099483.
(Continued)

*Primary Examiner* — Don K Wong
(74) *Attorney, Agent, or Firm* — Ostrolenk Faber LLP

(57) ABSTRACT

Embodiments of the present disclosure provide a method and an apparatus of correcting a collimator, which may correct a position of a collimator of a gamma knife apparatus. The method includes: separately obtaining a projection image of rays sequentially passing through collimation holes and an isocenter plane in the collimator in cases where the collimator moves to M positions; determining a target position with a highest degree of alignment of the collimator from the M positions according to obtained projection images of rays; recording position parameters corresponding to the target position, so as to control the collimator to move to the target position in a case where the a gamma knife apparatus is used for treatment.

16 Claims, 6 Drawing Sheets

(58) Field of Classification Search
CPC .... A61N 2005/1091; A61N 2005/1052; A61N 1/00; A61N 5/00; A61N 5/10; A61N 2005/1048; A61N 5/1064; A61N 5/1001; A61N 5/1027
See application file for complete search history.

(56) References Cited

U.S. PATENT DOCUMENTS

| | | | |
|---|---|---|---|
| 2012/0105969 | A1 | 5/2012 | Ehringfeld |
| 2016/0361567 | A1 | 12/2016 | Chappelow et al. |
| 2017/0209106 | A1 | 7/2017 | Ikhlef |
| 2017/0225015 | A1 | 8/2017 | Thieme et al. |
| 2018/0133518 | A1* | 5/2018 | Harper ................. A61N 5/1045 |

FOREIGN PATENT DOCUMENTS

| | | |
|---|---|---|
| CN | 102526885 A | 7/2012 |
| CN | 203436706 U | 2/2014 |
| CN | 104586415 A | 5/2015 |
| CN | 105288870 A | 2/2016 |
| CN | 105476654 A | 4/2016 |
| CN | 106908457 A | 6/2017 |
| CN | 107041997 A | 8/2017 |
| CN | 107297031 A | 10/2017 |
| CN | 107800026 A | 3/2018 |
| CN | 108186035 A | 6/2018 |
| CN | 108211134 A | 6/2018 |
| WO | WO 2013/182928 A1 | 12/2013 |

OTHER PUBLICATIONS

Written Opinion dated May 9, 2019 in corresponding PCT International Application No. PCT/CN2018/099483.

Chinese Office Action, dated Jan. 19, 2021, issued in corresponding Chinese Patent Application No. 201880008605.1. English translation. Total 19 pages.

Sun Xinchen, et al., "Quality Assurance Specifications For Tumor Radiotherapy Equipment and Techniques", Twelve Collimator Parallelism/Symmetry, pp. 108-109. Nanjing: Southeast University Press. (Dec. 2017). English translation.

* cited by examiner

METHOD AND APPARATUS OF CORRECTING COLLIMATOR OF RADIOTHERAPY EQUIPMENT

CROSS-REFERENCE TO RELATED APPLICATION

This application is a Bypass Continuation-in-part Application of PCT/CN2018/099483 filed Aug. 8, 2018, which is incorporated herein by reference in its entirety.

TECHNICAL FIELD

The disclosure relates to the field of medical instruments, and in particular, to a method and an apparatus of correcting a collimator of radiotherapy equipment.

BACKGROUND

At present, radiation therapy with a gamma knife apparatus has become an important means of treating tumors. A principle of the gamma knife apparatus is to use a collimator to make gamma rays emitted by radiation sources emitted from collimation holes in the collimator and focused to a focus, thereby killing diseased cells at the focus.

SUMMARY

Embodiments of the present disclosure provide a method and an apparatus of correcting a collimator of radiotherapy equipment, which may correct a position of a collimator of a gamma knife apparatus.

In order to achieve the above objective, embodiments of the present disclosure adopt the following technical solutions.

In a first aspect, embodiments of the present disclosure provide a method of correcting a collimator of radiotherapy equipment, and the method includes: separately obtaining a projection image of rays sequentially passing through collimation holes in the collimator and an isocenter plane of the radiotherapy equipment in cases where the collimator moves to M positions, wherein the M positions include a design position of the collimator and at least one other position where a displacement difference from the design position is less than a preset distance, and the design position is a theoretical position of alignment of the collimator; determining a target position with a highest degree of alignment of the collimator from the M positions according to obtained projection images of rays; and recording position parameters corresponding to the target position, so as to control the collimator to move to the target position in a case where using radiotherapy equipment for treatment.

Optionally, determining the target position with the highest degree of alignment of the collimator from the M positions according to the projection images of rays includes: determining the target position with the highest degree of alignment of the collimator from the M positions according to gray values and penumbra values of the projection images of rays.

Optionally, determining the target position with the highest degree of alignment of the collimator from the M positions according to gray values and penumbra values of the projection images of rays includes: generating isodose curves of a first percentage, isodose curves of a second percentage, and isodose curves of a third percentage of the rays according to the gray values and the penumbra values of the projection images of rays separately for the M positions to which the collimator moves. The second percentage is a half of a sum of the first percentage and the third percentage; the isodose curves of the second percentage are isodose curves of 50%; calculating a similarity T between each isodose curve of the second percentage of the rays and a corresponding theoretical isodose curve of the second percentage separately for the M positions to which the collimator moves; and determining the target position according to calculated similarities T and calculated distances L.

Optionally, determining the target position with the highest degree of alignment of the collimator from the M positions according to the projection images of rays, includes: generating isodose curves of a first percentage, isodose curves of a second percentage, and isodose curve of a third percentage of the rays according to the projection image of rays separately for the M positions to which the collimator moves. The second percentage is a half of a sum of the first percentage and the third percentage; the isodose curves of the second percentage are isodose curves of 50%; calculating a similarity T between each isodose curve of the second percentage of the rays and a corresponding theoretical isodose curve of the second percentage separately for the M positions to which the collimator moves; calculating a distance L between each isodose curve of the first percentage and a corresponding isodose curve of the third percentage of the rays separately for the M positions to which the collimator moves; and determining the target position according to calculated similarities T and calculated distances L.

Optionally, generating the isodose curves of the first percentage, the isodose curves of the second percentage, and the isodose curves of the third percentage of the rays according to the projection image of rays separately for the M positions to which the collimator moves, includes: generating the isodose curves of the first percentage, the isodose curves of the second percentage, and the isodose curves of the third percentage of the rays according to gray values of the projection images of rays separately for the M positions to which the collimator moves.

Optionally, determining the target position according to the calculated similarities T and the calculated distances L, includes: calculating alignment parameters q of the collimation holes corresponding to the projection images of rays according to the similarities T and the distances L separately for the M positions to which the collimator moves; calculating a total alignment parameter Q by taking a weighted average of the alignment parameters q of the collimation holes corresponding to the projection image of rays separately for the M positions to which the collimator moves; and determining a position at which the total alignment parameter Q is the largest among the M positions as the target position.

Optionally, the radiotherapy equipment includes radiation sources and the collimator, the collimator includes the collimation holes, and rays emitted from the radiation sources are focused to an isocenter of the radiotherapy equipment through the collimation holes.

In a second aspect, the embodiments of the present disclosure provide another apparatus of correcting the collimator of the radiotherapy equipment, and the apparatus includes a communication interface configured to receive projection images of rays each sequentially passing through collimation holes in the collimator and an isocenter plane of the radiotherapy equipment in cases where the collimator moves to M positions, wherein the M positions include a design position of the collimator and at least one other position where a displacement difference from the design position is less than a preset distance, and the design position is a theoretical position of alignment of the collimator; and a processor connected to the communication interface, wherein the processor is configured to determine a target position with a highest degree of alignment of the collimator from the M positions according to obtained projection images of rays, and record position parameters corresponding to the target position.

Optionally, the processor is configured to determine the target position with the highest degree of alignment of the collimator from the M positions according to gray values and penumbra values of the projection images of rays.

Optionally, the processor is configured to generate isodose curves of a first percentage, isodose curves of a second percentage, and isodose curves of a third percentage of the rays according to the projection image of rays separately for the M positions to which the collimator moves, wherein the second percentage is a half of a sum of the first percentage and the third percentage; the isodose curves of the second percentage are isodose curves of 50%; calculate a similarity T between each isodose curve of the second percentage of the rays and a corresponding theoretical isodose curve of the second percentage separately for the M positions to which the collimator moves; calculate a distance L between each isodose curve of the first percentage and a corresponding isodose curve of the third percentage of the rays separately for the M positions to which the collimator moves; and determine the target position according to calculated similarities T and calculated distances L.

Optionally, the processor is configured to generate the isodose curves of the first percentage, the isodose curves of the second percentage, and the isodose curves of the third percentage of the rays according to gray values of the projection image of rays separately for the M positions to which the collimator moves.

Optionally, the processor is configured to calculate alignment parameters q of the collimation holes corresponding to the projection image of rays according to the similarities T and the distances L separately for the M positions to which the collimator moves; calculate a total alignment parameter Q by taking a weighted average of the alignment parameters q of the collimation holes corresponding to the projection image of rays separately for the M positions to which the collimator moves; and determine a position at which the total alignment parameter Q is the largest among the M positions as the target position.

The apparatus further includes a memory configured to store program codes and data of the apparatus of correcting the collimator of the radiotherapy equipment, and a bus connected the processor to the memory via the bus.

Optionally, the radiotherapy equipment further includes radiation sources; the collimator includes the collimation holes, and the collimation holes are configured such that rays emitted from the radiation sources are focused to an isocenter of the radiotherapy equipment.

In a third aspect, the embodiments of the present disclosure provide a non-transitory computer storage medium, and the computer storage medium includes instructions that, when run on a computer, cause the computer to execute the method of correcting the collimator of the radiotherapy equipment according to the first aspect.

In a fourth aspect, the embodiments of the present disclosure provide a computer program product, and the computer program product includes instructions that, when run on a computer, cause the computer to execute the method of correcting the collimator of the radiotherapy equipment according to the first aspect.

In the embodiments of the present disclosure, the projection image of rays is received by a ray detector separately in cases where the collimator is at a design position before a correction of the collimator and M positions near the design position, and a target position with the highest degree of alignment of the collimator is selected according to the projection images of rays, and a target position with the highest degree of alignment of the collimator is selected from the M positions and recorded according to the projection images of rays, so that the collimator may be driven to the target position when a next treatment with the gamma knife apparatus is performed to achieve a correction of the position of the collimator during treatment. Rays at the isocenter are more concentrated, which allows patients to receive a greater dose at tumors and a lesser dose at non-tumors.

BRIEF DESCRIPTION OF THE DRAWINGS

In order to describe technical solutions in embodiments of the present disclosure or the prior art more clearly, the drawings to be used in the description of the embodiments will be briefly described below. Obviously, the drawings to be described below are merely some embodiments of the present disclosure, and a person of ordinary skill in the art may obtain other drawings according to these drawings without paying any creative effort.

DETAILED DESCRIPTION

Figure 1:
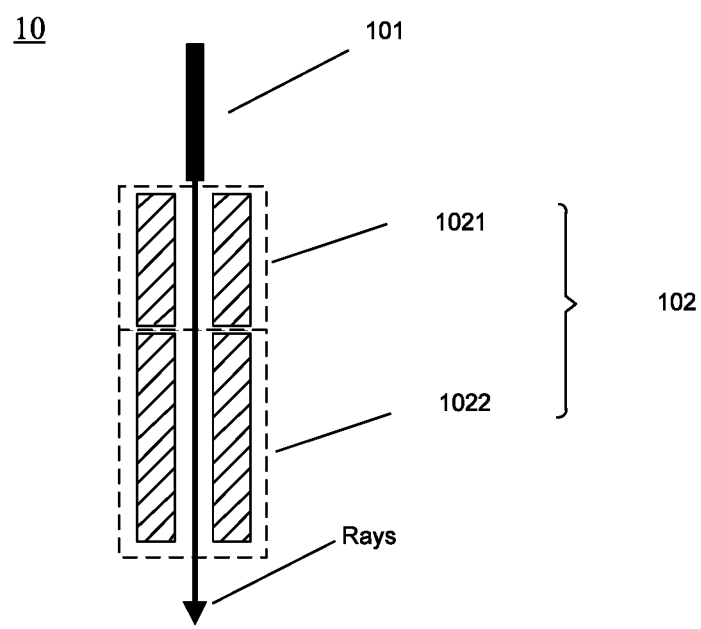
FIG. 1 is a schematic diagram showing a structure of a focusing treatment head in a gamma knife apparatus.

The technical solutions in the embodiments of the present disclosure will be described clearly and completely with reference to the accompanying drawings in the embodiments of the present disclosure. Obviously, the described embodiments are merely some but not all of embodiments of the present disclosure. All other embodiments made on the basis of the embodiments of the present disclosure by a person of ordinary skill in the art without paying any creative effort shall be included in the protection scope of the present disclosure.

For example, the terms "unit", "component", "module", "system" and the like used in the present disclosure are intended to mean a computer-related entity, which may be a hardware, a firmware, a combination of hardware and software, a software or a running software. For example, a component may be, but is not limited to a process running on a processor, a processor, an object, an executable file, a thread in execution, a program, and/or a computer. As an example, both an application running on a computing device and the computing device may be components. One or more components may exist in a process and/or a thread in execution, and the components may be located in a computer and/or distributed in two or more computers. In addition, these components can be executed in various computer readable media with various data structures thereon. These components can communicate in a local and/or remote process, for example, by signals having one or more data packets (for example, data from one component, and the component communicates with another component in the local system, the distributed system, and/or communicates with other systems via a network such as the Internet by means of signals).

The present disclosure will present various aspects, embodiments, or features involving a system that may include a plurality of devices, components, modules, and the like. It will be understood and appreciated that each system may include other devices, components, modules and the like, and/or may not include all of the devices, components, modules and the like discussed in combination with the drawings. In addition, a combination of these solutions may also be used.

In addition, in the embodiments of the present disclosure, the word "for example" is used to mean an example, an illustration, or a description. Any embodiment or design solution described as "example" in the present disclosure should not be construed as more preferred or advantageous over other embodiments or design solutions. More exactly, the term "for example" is used to present a concept in a concrete manner.

In the embodiments of the present disclosure, information, signal, and message may sometimes be used interchangeably. It will be noted that the meaning thereof to be expressed is consistent in a case where the distinction is not emphasized. "Of", "corresponding" and "relevant" may sometimes be used interchangeably. It will be noted that the meaning thereof to be expressed is consistent in a case where the distinction is not emphasized.

In order to facilitate the clear description of the technical solutions of the embodiments of the present disclosure, the words "first", "second" and the like are used to distinguish the same items or similar items with essentially the same function and effect in the embodiments of the present disclosure. Those skilled in the art may understand that the words "first" and "second" are not limited to the quantity and the execution order.

First, the technical terms involved in the present disclosure are introduced.

The gamma knife is a main treatment means for stereotactic radiosurgery. In this treatment means, an intracranial diseased tissue is selectively determined as a target according to the principle of stereotactic geometry, and gamma rays generated by cobalt-60 are used for one-time large-dose focused irradiation to cause the intracranial diseased tissue to undergo focal necrosis or functional change, thereby achieving a purpose of treating diseases. A treatment principle of the gamma knife is similar to a focused process of a magnifier. If the magnifier is put in the sun, a dazzling light spot, i.e., the focus, will be formed under the magnifier. Outside the focus, human's feeling is as usual, however, there is a high heat enough to ignite some objects at the focus.

In some gamma knife apparatuses, it is necessary to use a motor to drive the collimator to move to a predetermined position during treatment, so that the collimation holes in the collimator are aligned with the radiation sources.

Inventors of the present disclosure have found that, due to a decrease in accuracy of the drive motor caused by an increase of the number of uses of the gamma knife apparatus, and improper operation in use, the collimator offset problem occurs. As a result, the collimation holes in the collimator and the radiation sources may not be precisely aligned, thereby a focused penumbra at the focus is too large, and the dose has a deviation. Therefore, a method is needed to correct a position of the collimator of the gamma knife apparatus.

Figure 2:
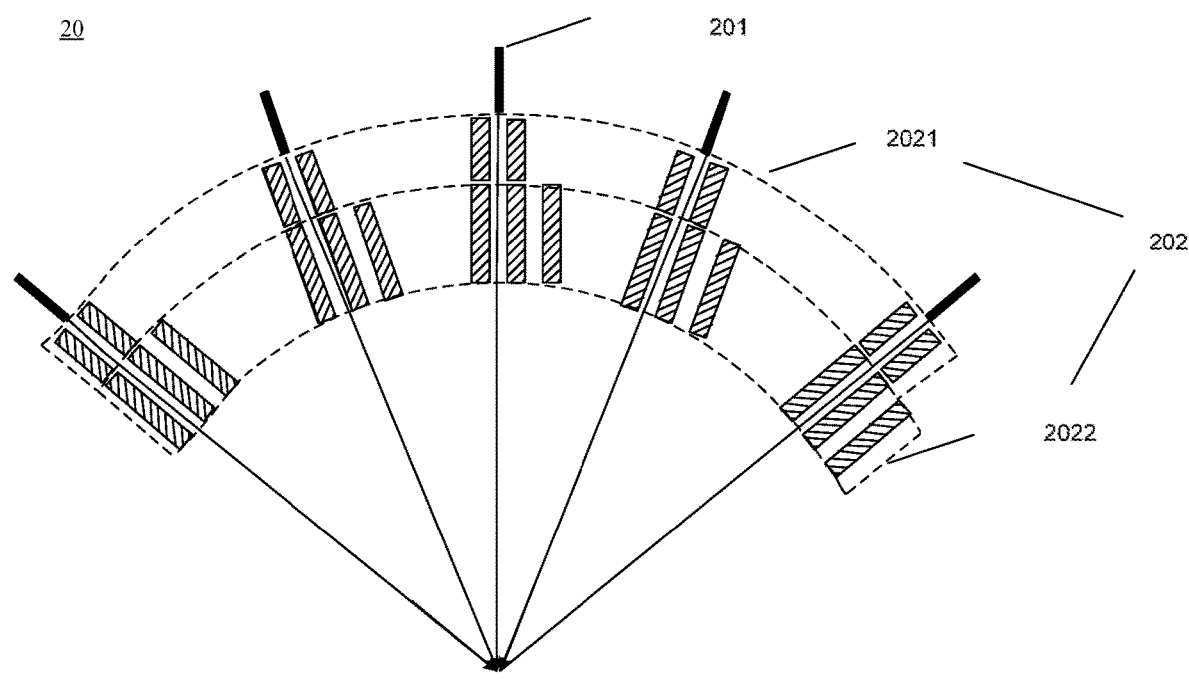
FIG. 2 is a schematic diagram showing a structure of a gamma knife apparatus.

The gamma knife apparatus is radiotherapy equipment that uses the gamma knife treatment means for treatment. The focusing treatment head emits rays from different directions to human tissues, and the rays are focused at the target (focus), so that an irradiation dose at the target is sufficient to kill the diseased tissue, while other human tissues are only irradiated with a small dose and thus are not damaged. FIG. 1 is a schematic diagram showing a structure of a focusing treatment head 10 in a gamma knife apparatus. The focusing treatment head 10 includes a radiation source 101 and a collimator 102. During treatment, rays emitted by the radiation source 101 will propagate in a predetermined propagation direction after passing through the collimation hole of the collimator 102. As shown in FIG. 1, the collimator 102 may include a pre-collimator 1021 and a final collimator 1022. The pre-collimator 1021 is fixed relative to the radiation source in a mechanical structure, and the final collimator 1022 may include a plurality of sets of final collimation holes each with a different aperture to form radiation fields with different sizes at the focus. One set of the plurality of sets of final collimation holes with different apertures is aligned with the pre-collimator 1021 by means of rotation of a motor during a treatment, so as to kill tumor tissues at the focus. In addition, only the structures of the radiation source and the collimation hole corresponding to one beam in the focusing treatment head are shown in FIG. 1, however, in practical applications, the focusing treatment head in the gamma knife apparatus includes a plurality of beams. For example, FIG. 2 is a schematic diagram showing a structure of a focusing treatment head 20, and the focusing treatment head 20 includes radiation sources 201 and a collimator 202. The collimator 202 includes a pre-collimator 2021 and final collimator sets 2022. There are five pre-collimation holes in the pre-collimator 2021. The final collimator sets 2022 include two final collimation hole sets, and each final collimation hole set includes five final collimation holes. By rotating the final collimator sets 2022 during treatment, one of the two final collimation hole sets in the final collimator sets 2022 is aligned with the pre-collimated holes, so that the rays pass through the pre-collimation holes and the final collimation holes to form a radiation field. For example, the final collimator sets 2022 is rotated clockwise to align a final collimation hole set on the left with the pre-collimator, and the collimator is in a state shown in FIG. 2. The final collimator sets 2022 may also be rotated counterclockwise to align a final collimation hole set on the right with the pre-collimator. It will be noted that the number of the collimation holes in the collimator in the focusing treatment head shown in FIG. 2 is only an example.

The number of the collimation holes may be designed according to requirements in a specific application, which is not limited in the present disclosure.

The principle of the present disclosure is described below. In the existing gamma knife apparatus, mechanical and electrical designs and a grating ruler are typically utilized to ensure alignment of the radiation sources and the collimator. In a case of verifying whether the radiation sources and the collimator are aligned, a film is placed at an isocenter, the collimator is turned on to expose the film, and the image presented on the film is used to verify an overall degree of focus of the gamma knife apparatus. By using this verification method, an alignment situation of one of the collimation holes may not be obtained, and an adjustment of the collimator may not be effectively guided. Therefore, there is currently no effective method of correcting the collimator in the prior art. The present disclosure provides a method and an apparatus of correcting a collimator, which may automatically complete a correction of the collimator and improve a treatment effect of the gamma knife apparatus.

Isodose curves are the lines joining the points of equal percentage depth dose (PDD). The curves are usually drawn at regular intervals of absorbed dose and expressed as a percentage of the dose at a reference point.

Based on the above inventive principle, embodiments of the present disclosure provide a method of correcting a collimator of radiotherapy equipment. The method is applied to radiotherapy equipment. The radiotherapy equipment in the embodiments of the present disclosure may be a gamma knife apparatus, or radiotherapy equipment that uses other rays for treatment and in which the collimator needs to be corrected, which is not limited in the present disclosure.

Figure 3:
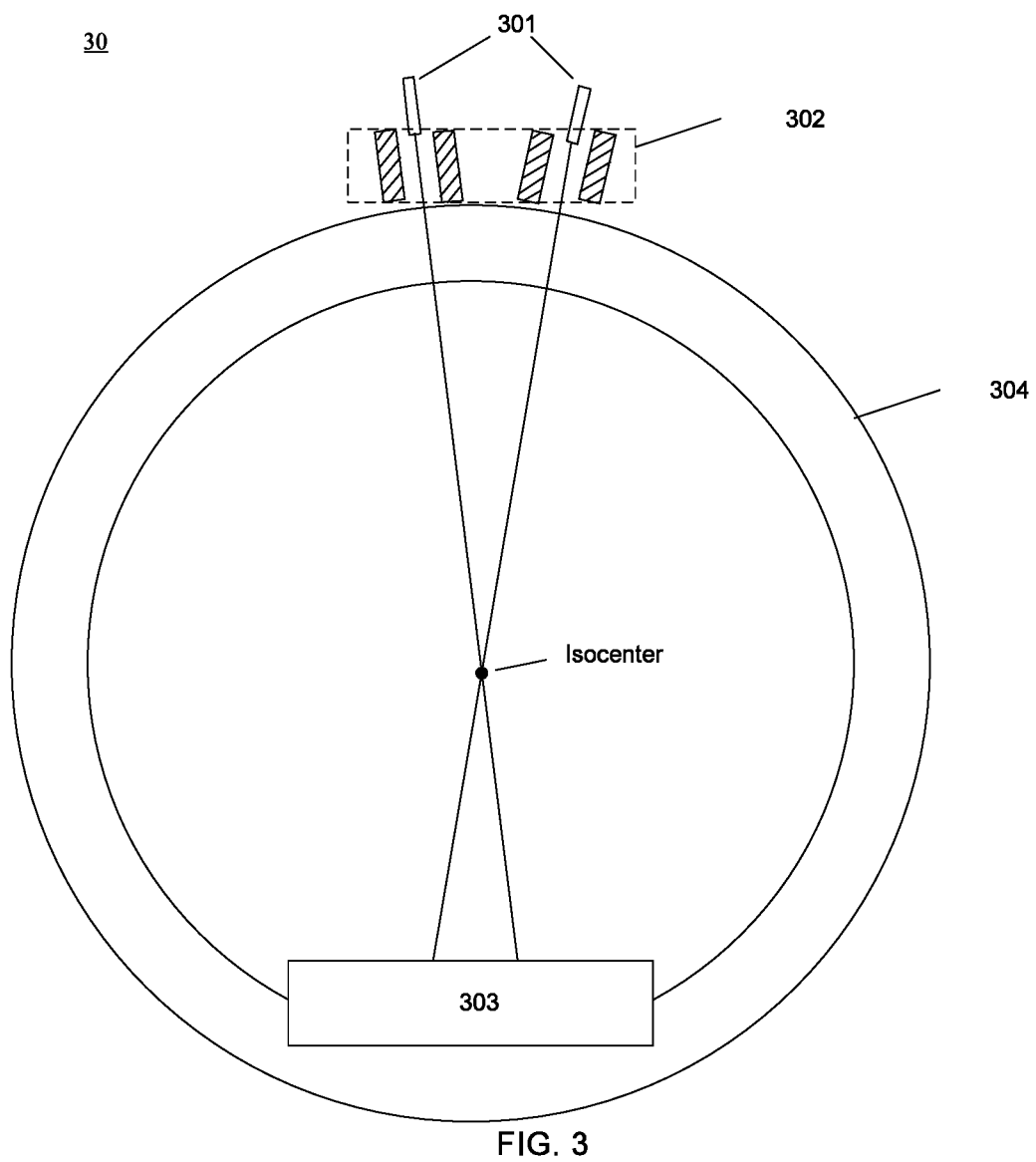
FIG. 3 is a schematic diagram showing a structure of a gamma knife apparatus, in accordance with embodiments of the present disclosure.

As shown in FIG. 3, the radiotherapy equipment 30 includes a focusing treatment head, and the focusing treatment head includes radiation sources 301 and a collimator 302. It will be noted that the radiation sources 301 and two collimation holes in the collimator 302 are merely drawn up exemplarily in FIG. 3. In actual radiotherapy equipment, the number of collimation holes in the collimator 302 may be set according to actual needs, as long as the rays emitted by the radiation sources are emitted at different angles and focused at the isocenter.

As shown in FIG. 3, the focusing treatment head is disposed on a roller 304. The focusing treatment head is rotatable with a rotation of the roller 304. The collimator 302 is movable within a predetermined position range relative to the radiation sources 301. As shown in FIG. 3, in a case where the collimator moves to the predetermined position range, the radiation sources 301 generate at least one beam and the at least one beam is directed to the isocenter through at least one collimation hole. In addition, the radiotherapy equipment 30 may further include a ray detector 303. As shown in FIG. 3, the ray detector 303 may be disposed at a position on the roller 304 opposite the focusing treatment head, so that the rays may be irradiated on the ray detector 303 after passing through the at least one collimation hole in the collimator and the isocenter of the radiotherapy equipment. Thereby, by using the ray detector 303, the projection images of rays passing through the at least one collimation hole in the collimator and the isocenter of the radiotherapy equipment may be obtained.

The collimator 302 in the embodiments of the present disclosure refers to a generic designation of any collimation component having at least one collimation hole set and capable of aligning one collimation hole set with the radiation sources by means of motion. For example, in a case where the radiotherapy equipment shown in FIG. 2 includes a pre-collimator 2021 that is relatively fixed and final collimator sets 2022 that are movable, the collimator 302 in the embodiments of the present disclosure refers to the final collimator sets 2022.

Figure 4:
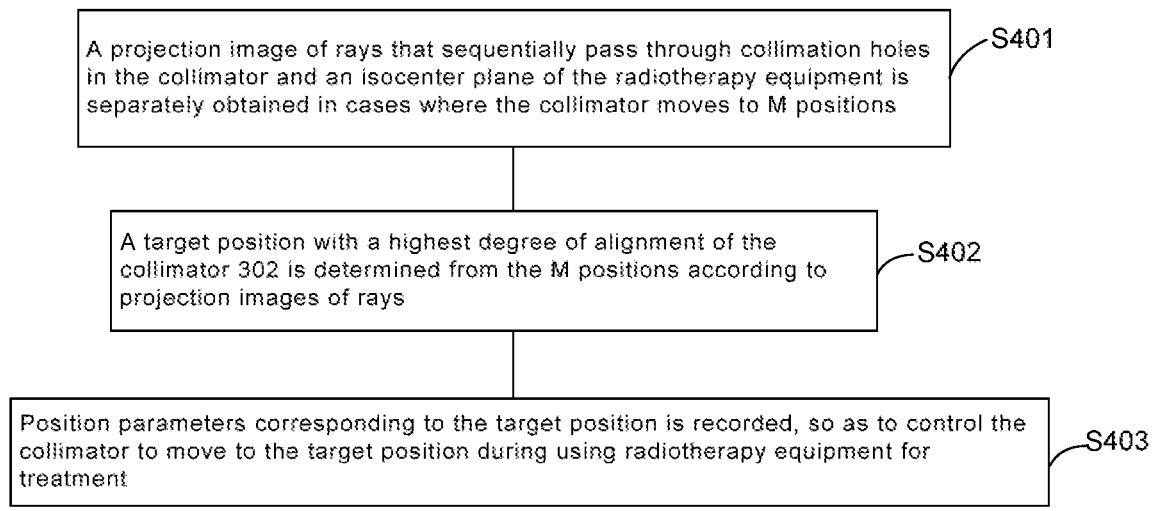
FIG. 4 is a flow diagram of a method of correcting a collimator of radiotherapy equipment, in accordance with embodiments of the present disclosure.

As shown in FIG. 4, the method of correcting a collimator of radiotherapy equipment includes the following steps.

In S401, a projection image of rays that sequentially pass through collimation holes in the collimator and an isocenter plane of the radiotherapy equipment is separately obtained in cases where the collimator moves to M positions.

It will be noted that the "isocenter plane of the radiotherapy equipment" in the embodiments of the present disclosure refers to a plane where the isocenter of the radiotherapy equipment is located and which is perpendicular to a line connected the treatment head to the ray detector.

The M positions include: a design position of the collimator 302 and at least one other position where a displacement difference from the design position is less than a preset distance. The design position is a theoretical position of alignment of the collimator 302. In a case where the collimator includes pre-collimators and final collimators, the design position is a theoretical position where the pre-collimator and the final collimator are aligned. In a case where the collimator includes the final collimator, the design position is a theoretical position where the final collimator is aligned with the radiation source.

For example, in the design position (that is, a position of the final collimator aligned with the radiation source obtained during designing the collimator structure before correction), the collimator 302 is finely adjusted by the motor, and the collimator 302 is shifted to left by 0.5 mm and 1 mm from the design position, and then shifted to right by 0.5 mm and 1 mm from the design position.

Then, the projection image of rays received by the radiation detector is separately obtained in cases where the collimator 302 is moved to five positions, i.e., the design position, a position shifted 0.5 mm to the left from the design position, a position shifted 1 mm to the left from the design position, a position shifted 0.5 mm to the right from the design position, and a position shifted 1 mm to the right from the design position.

In S402, a target position with a highest degree of alignment of the collimator 302 is determined from the M positions according to projection images of rays.

The target position with the highest degree of alignment of the collimator may be determined from the M positions according to gray values and penumbra values of the projection images of rays.

For example, a projection image with the smallest penumbra and the largest gray scale is selected from M projection images obtained respectively in cases where the collimator 302 is located at the M positions, and the position corresponding to the projection image is taken as the target position. In a case where the target position is determined according to the gray values and the penumbra values of the projection images of rays, different weight ratios may be set for the penumbra value and the gray value according to an influence of the penumbra value and the gray value on the degree of alignment of the collimator. For example, a weight of the penumbra value is set to 80%, and a weight of the gray value is set to 20%. The specific weight is not limited by the present disclosure.

In S403, position parameters corresponding to the target position is recorded, so as to control the collimator to move to the target position during using radiotherapy equipment for treatment.

After determining the target position, information about the target position or drive parameters of a servo motor corresponding to the target position may be recorded in a configuration file of the radiotherapy equipment. Then, when the radiotherapy equipment is used for treatment, the servo motor may be controlled to rotate according to the information about the target position or the drive parameters, thereby driving the collimator 302 to move to the target position.

In the embodiments of the present disclosure, the projection image of rays is received by the ray detector separately in cases where the collimator is at the design position before a correction of the collimator and a plurality of positions near the design position, and a target position with the highest degree of alignment of the collimator is selected according to the projection images of rays, thereby achieving a correction of the position of the collimator according to the selected target position. In addition, rays at the isocenter may be more concentrated, which allows patients to receive a greater dose at tumors and a lesser dose at non-tumors.

Figure 5:
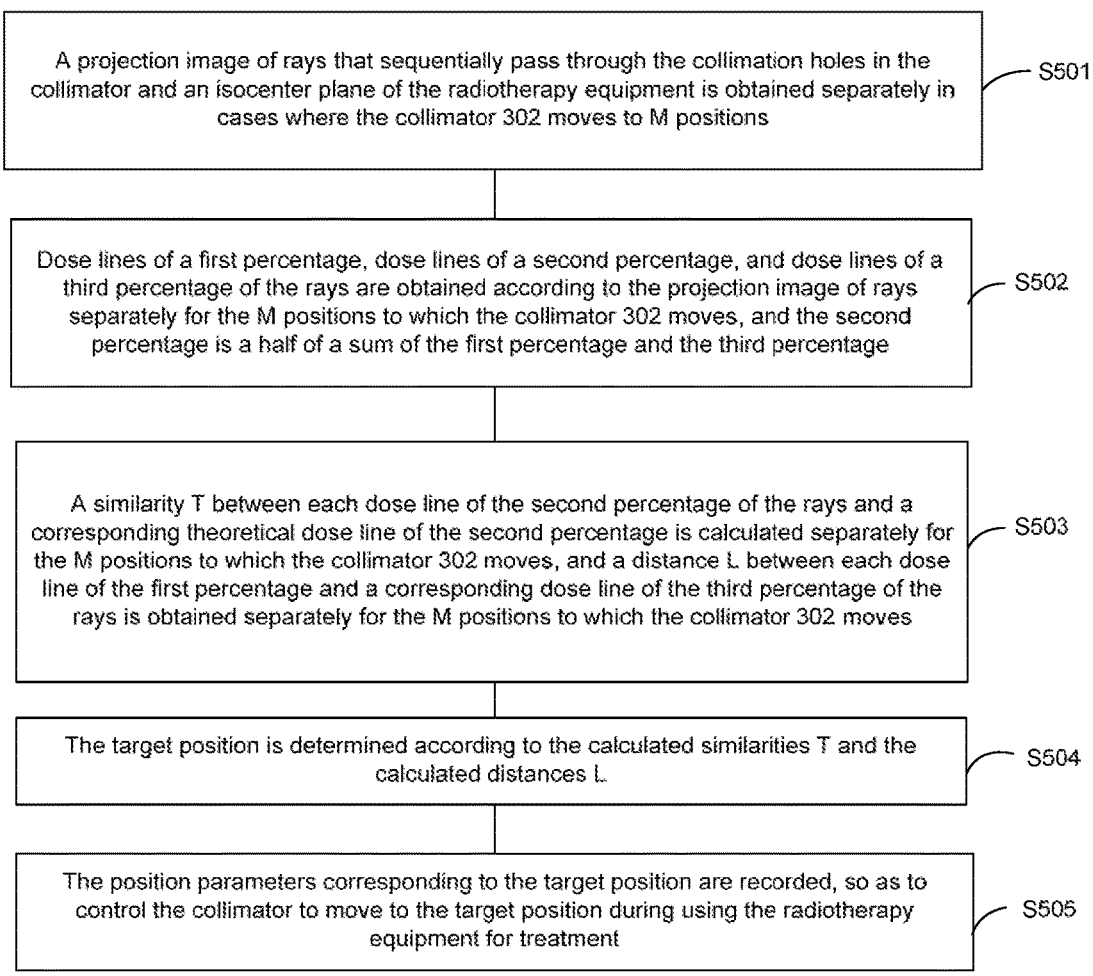
FIG. 5 is a flow diagram of another method of correcting a collimator of radiotherapy equipment, in accordance with embodiments of the present disclosure.

In an embodiment, in a case where the target position with the highest degree of alignment of the collimator is determined from the M positions according to the projection images of rays, the target position may be calculated and determined according to similarities each between an isodose curve of the rays and a theoretical isodose curve, and relevant parameters of degree of focus of the rays to achieve the correcting method shown in FIG. 4. The embodiments of the present disclosure further provide a method of correcting the collimator of the radiotherapy equipment, and as an example of the correcting method shown in FIG. 4, the method is used in the radiotherapy equipment. The gamma knife apparatus used in the method may refer to the above description of the gamma knife apparatus, and the repeated description will not be described. As shown in FIG. 5, the method includes the following steps.

In S501, a projection image of rays that sequentially pass through the collimation holes in the collimator and an isocenter plane of the radiotherapy equipment is obtained separately in cases where the collimator 302 moves to M positions.

For example, it is assumed that the focusing treatment head includes five radiation sources 301, the collimator 302 includes a single set of collimation holes, and the set of collimation holes include five collimation holes. A projection image of five rays that pass through the collimation holes in the collimator and the isocenter plane of the radiotherapy equipment is obtained separately in cases where the collimator 302 is moved to the five positions, i.e., the design position, a position shifted 0.5 mm to the left from the design position, a position shifted 1 mm to the left from the design position, a position shifted 0.5 mm to the right from the design position, and a position shifted 1 mm to the right from the design position, thereby obtaining five projection images of rays, each of which includes projections of five rays.

In S502, isodose curves of a first percentage, isodose curves of a second percentage, and isodose curves of a third percentage of the rays are obtained according to the projection image of rays separately for the M positions to which the collimator 302 moves, and the second percentage is a half of a sum of the first percentage and the third percentage.

The isodose curves of the first percentage, the isodose curves of the second percentage, and the isodose curves of the third percentage of the rays may be generated according to the gray values of the projection image of rays obtained separately in cases where the collimator 302 moves to the M positions.

A dose-gray value function may be fitted according to a corresponding relationship curve between doses and gray values of the projection image. Then, an isodose curve of the first percentage, an isodose curve of the second percentage and an isodose curve of the third percentage of the rays are fitted in the projection image according to gray values corresponding to the dose of the first percentage, the dose of the second percentage, and the dose of the third percentage of the rays.

In an embodiment, in order to obtain a better detection result, the first percentage, the second percentage, and the third percentage in the embodiments of the present disclosure may be respectively set as 20%, 50%, and 80%.

In S503, a similarity T between each isodose curve of the second percentage of the rays and a corresponding theoretical isodose curve of the second percentage is calculated separately for the M positions to which the collimator 302 moves, and a distance L between each isodose curve of the first percentage and a corresponding isodose curve of the third percentage of the rays is obtained separately for the M positions to which the collimator 302 moves according to the projection image of rays.

Figure 9:
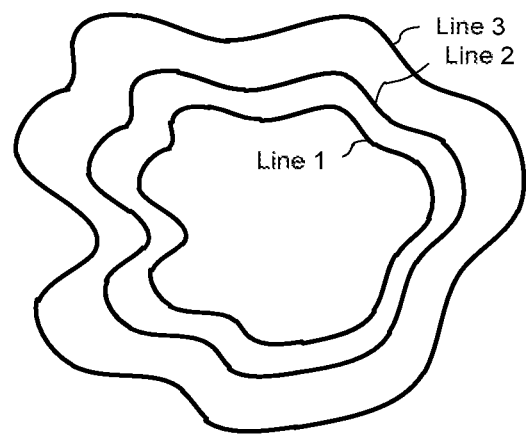
FIG. 9 is a diagram of an isodose curve of rays at a position of M positions.

In each of the M positions, an isodose curve diagram of the rays may be obtained. The isodose curve diagram is shown in FIG. 9. In FIG. 9, in a case where the line 1 is the isodose curve of the first percentage, the line 2 is the isodose curve of the second percentage, and the line 3 is the isodose curve of the third percentage, the distance between two isodose curves may be understood as any one of an average distance, the minimum distance, the maximum distance and the like between two lines.

In S504, the target position is determined according to the calculated similarities T and the calculated distances L.

Since the higher the similarity between the isodose curve and the theoretical isodose curve of the rays is, the closer to an ideal position the position of the corresponding collimation hole is. In addition, the smaller the distance between the isodose curves is, the more concentrated the focusing at the isocenter is. In this way, in cases where the higher the similarity between the isodose curve and the theoretical isodose curve of the rays is or the smaller the distance between the isodose curves is, the patient may receive greater doses at the tumor and smaller doses at the non-tumor. Therefore, in the embodiments of the present disclosure, the similarity T and the distance L are used to determine the target position, so that the correction effect is better.

In an implementation manner, step S504 includes the following processes.

In S5041, alignment parameters q of the collimation holes corresponding to the projection image of rays are calculated according to the similarities T and the distances L separately for the M positions to which the collimator moves.

The alignment parameter q is a measure of the degree of alignment, and has a maximum value of 100% and a minimum value of 0. In a case where the distance L is constant, the similarity T is larger, and the corresponding alignment parameter q is larger. In a case where the similarity T is constant, the distance L is smaller, and the corresponding alignment parameter q is larger.

In a case where the target position is determined according to the similarities T and the distances L, the similarity T and the distance L may be set to different weight ratios according to an influence of the similarity T and the distance L on the degree of alignment of the collimator. For example, a weight of the similarity T is set to 80%, and a weight of the distance L is set to 20%. The specific weight is not limited by the present disclosure.

In S5042, a total alignment parameter Q is calculated by taking a weighted average of the alignment parameters q of the collimation holes corresponding to the projection image of rays separately for the M positions to which the collimator moves.

In S5043, a position at which the total alignment parameter Q is the largest among the M positions is selected as the target position.

For example, the collimator 302 includes five collimation holes. The collimator 302 is rotated to two positions 0.5 mm and 1.0 mm on the left side of the design position and the projection images are obtained. Measurement results are shown in table 1 and table 2 below. Table 1 shows values of the similarities T, the distances L, and the alignment parameters q of the five collimation holes in a case where the collimator 302 is at the position of 0.5 mm on the left side of the design position. Table 2 shows values of the similarities T, the distances L, and the finally calculated alignment parameters q of the five collimation holes in a case where the collimator 302 is at the position of 1.0 mm on the left side of the design position.

TABLE 1

|  | First collimation hole | Second collimation hole | Third collimation hole | Fourth collimation hole | Fifth collimation hole |
| --- | --- | --- | --- | --- | --- |
| Similarity T | 80% | 75% | 85% | 80% | 90% |
| Distance L | 1 mm | 2 mm | 0.8 mm | 1 mm | 0.6 mm |
| Alignment parameter q | 80% | 67% | 85% | 80% | 89% |

TABLE 2

|  | First collimation hole | Second collimation hole | Third collimation hole | Fourth collimation hole | Fifth collimation hole |
| --- | --- | --- | --- | --- | --- |
| Similarity T | 90% | 85% | 85% | 92% | 88% |
| Distance L | 0.6 mm | 0.8 mm | 0.8 mm | 0.5 mm | 0.7 mm |
| Alignment parameter q | 89% | 85% | 85% | 91% | 88% |

Further, the total alignment parameter Q of the collimator 302 at the position 0.5 mm on the left side of the design position may be calculated (in table 1, the weights of the alignment parameters q may be the same or may not):

(80%+67%+85%+80%+89%)/5=80.2%

The total alignment parameter Q of the collimator 302 at the position 1.0 mm on the left side of the design position may be calculated (in table 2, the weights of the alignment parameters q may be the same or may not):

(89%+85%+85%+91%+88%)/5=87.6%

Therefore, the position 1.0 mm on the left side of the design position is written into a configuration file of the radiotherapy equipment as a position where the collimator 302 is optimally aligned.

In S505, the position parameters corresponding to the target position are recorded, so as to control the collimator to move to the target position during using the radiotherapy equipment for treatment.

Figure 6:
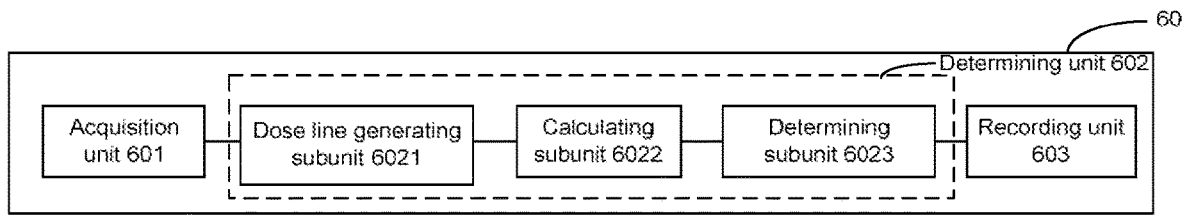
FIG. 6 is a schematic diagram showing a structure of an apparatus of correcting a collimator of radiotherapy equipment, in accordance with embodiments of the present disclosure.

On the other hand, based on the above described method of correcting the collimator of the radiotherapy equipment, embodiments of the present disclosure further provide an apparatus of correcting the collimator of the radiotherapy equipment. For example, an apparatus 60 of correcting the collimator of the radiotherapy equipment provided by the embodiments may be installed in the radiotherapy equipment, so that the collimator may be automatically corrected by the radiotherapy equipment regularly. The radiotherapy equipment in the embodiments may refer to the description of the above radiotherapy equipment, which will not be described here again. As shown in FIG. 6, the apparatus 60 of correcting the collimator of the radiotherapy equipment includes an acquisition unit 601, a determining unit 602, and a recording unit 603.

The acquisition unit 601 is used to obtain a projection image of rays sequentially passing through the collimation holes in the collimator and an isocenter plane of the radiotherapy equipment separately in cases where the collimator 302 moves to M positions. The M positions include: the design position of the collimator and at least one other position where the displacement difference from the design position is less than a preset distance. The design position is a theoretical position of alignment of the collimator.

The determining unit 602 is used to determine a target position with the highest degree of alignment of the collimator from the M positions according to obtained projection images of rays.

The recording unit 603 is used to record position parameters corresponding to the target position, so as to control the collimator to move to the target position during using the radiotherapy equipment for treatment.

Optionally, the determining unit 602 is used to determine the target position with the highest degree of alignment of the collimator from the M positions according to gray values and penumbra values of the projection images of rays.

Optionally, the determining unit 602 includes an isodose curve generating subunit 6021, a calculating subunit 6022, and a determining subunit 6023.

The isodose curve generating subunit 6021 is used to generate isodose curves of a first percentage, isodose curves of a second percentage, and isodose curves of a third percentage of the rays according to the projection image of rays separately for the M positions to which the collimator moves, and the second percentage is a half of a sum of the first percentage and the third percentage. In some embodiments, the isodose curves of the first percentage, the isodose curves of the second percentage, and the isodose curves of the third percentage may be generated according to the gray values of the projection image of rays.

The calculating subunit 6022 is used to calculate a similarity T between an isodose curve of the second percentage of the rays and a corresponding theoretical isodose curve of the second percentage according to the projection image of rays separately for the M positions to which the collimator moves, and calculate a distance L between an isodose curve of the first percentage and a corresponding isodose curve of the third percentage of the rays separately for the M positions to which the collimator moves.

The determining subunit 6023 is used to determine the target position according to similarities T and the distances L.

Optionally, the determining subunit 6023 is used to: calculate alignment parameters q of the collimation holes corresponding to the projection image of rays according to the similarities T and the distances L separately for the M positions to which the collimator moves, calculate a total alignment parameter Q by taking a weighted average of the alignment parameters q of the collimation holes corresponding to the projection image of rays separately for the M positions to which the collimator moves, and determine a position at which the total alignment parameter Q is the largest among the M positions as the target position.

The apparatus of correcting the collimator in the embodiments of the present disclosure may be applied to implement the method embodiments provided above. Therefore, technical effects that may be obtained by using the apparatus may also refer to the above method embodiments, which will not be described here again.

Figure 7:
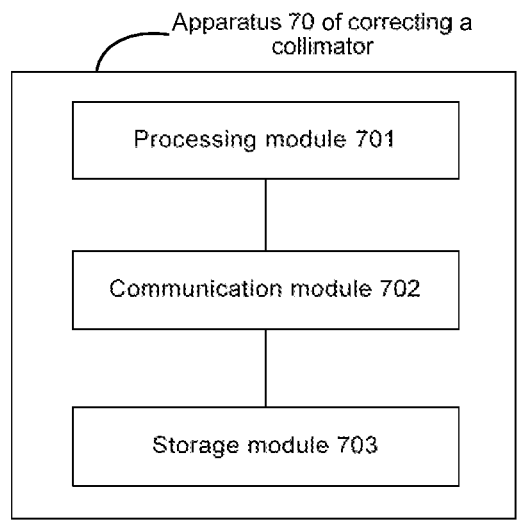
FIG. 7 is a schematic diagram showing a structure of another apparatus of correcting a collimator of radiotherapy equipment, in accordance with embodiments of the present disclosure.

In a case where an integrated unit is employed, FIG. 7 is a schematic diagram showing a possible structure of an apparatus of correcting the collimator of the radiotherapy equipment involved in the above embodiments. The apparatus 70 of correcting the collimator of the radiotherapy equipment includes a processing module 701 and a communication module 702. The processing module 701 is used to control and manage an action of the apparatus 70 of correcting the collimator of the radiotherapy equipment. For example, the processing module 701 is used to support the apparatus 70 of correcting the collimator of the radiotherapy equipment to execute steps, such as S402-S403 in FIG. 4 and S502-S505 in FIG. 5, and thus the processing module 701 achieves functions of the determining unit 602 and the recording unit 603 in FIG. 6. The communication module 702 is used to support communication between the apparatus 70 of correcting the collimator of the radiotherapy equipment and other physical devices. For example, the communication module 702 is used to communicate with the ray detector, and obtain, from the ray detector, the projection image of rays passing through the collimation holes in the collimator and the isocenter plane of the radiotherapy equipment, so as to complete the steps of S401 in FIG. 4 and S501 in FIG. 5, so that the communication module 702 achieves the function of the acquisition unit 601 in FIG. 6. The apparatus 70 of correcting the collimator of the radiotherapy equipment may further includes a storage module 703 for storing program codes and data of the apparatus 70 of correcting the collimator of the radiotherapy equipment.

The processing module 701 may be a processor or a controller, such as a central processing unit (CPU), a general-purpose processor, a digital signal processor (DSP), an application-specific integrated circuit (ASIC), a field programmable gate array (FPGA) or a programmable logic device, a transistor logic device, a hardware component, or any combination thereof. The processing module 701 may implement or carry out various illustrative logical blocks, modules and circuits described in combination with the content of the present disclosure. The processor may also be a combination to realize computing functions. For example, the processor is a combination including one or more microprocessors, a combination of the DSP and the microprocessor, or the like. The communication module 702 may be a transceiver, a transceiver circuit, or a communication interface. The storage module 703 may be a memory.

In a case where the processing module 701 is a processor, the communication module 702 is a communication interface, and the storage module 703 is a memory. The apparatus of correcting the collimator of the radiotherapy equipment involved in the embodiments of the present disclosure may be the apparatus of correcting a collimator of radiotherapy equipment shown in FIG. 8.

Figure 8:
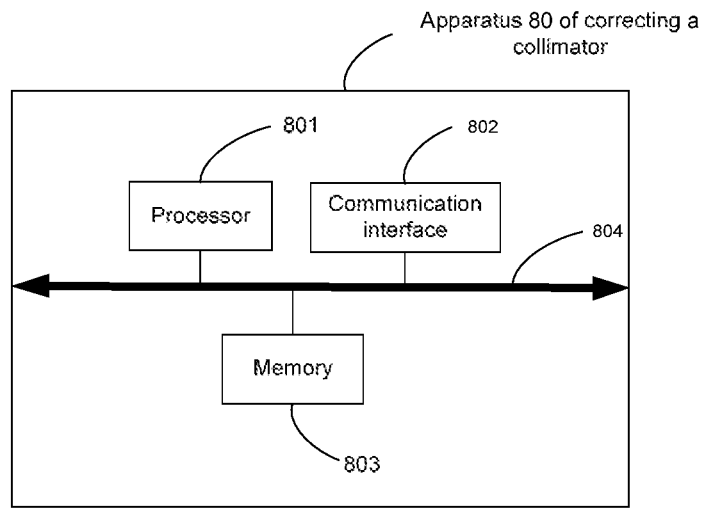
FIG. 8 is a schematic diagram showing a structure of yet another apparatus of correcting a collimator of radiotherapy equipment, in accordance with embodiments of the present disclosure.

Referring to FIG. 8, the apparatus 80 of correcting a collimator of radiotherapy equipment includes a processor 801, a communication interface 802, a memory 803, and a bus 804. The communication interface 802, the processor 801, and the memory 803 are connected to each other through the bus 804. The bus 804 may be a peripheral component interconnect (PCI) bus or an extended industry standard architecture (EISA) bus, or the like. The bus may be divided into an address bus, a data bus, a control bus, and the like. For ease of representation, only one thick line is shown in FIG. 8, but it does not mean that there is only one bus or one type of bus.

The steps of the method or the algorithms described in combination with the content of the present disclosure may be implemented in hardware, or may be implemented by a processor executing software instructions. The embodiments of the present disclosure further provide a storage medium, and the storage medium may include a memory 803 for storing computer software instructions used by the apparatus of correcting a collimator of the radiotherapy equipment, and the computer software instructions include program codes designed to perform the method of correcting the collimator of the radiotherapy equipment provided in the above embodiments. The software instructions may be composed of corresponding software modules, and the software modules may be stored in a random access memory (RAM), a flash memory, a read only memory (ROM), an erasable programmable ROM (EPROM), an electrically EPROM (EEPROM), a register, a hard disk, a mobile hard disk, a CD-ROM, or any other form of storage medium well known in the art. An exemplary storage medium is coupled to the processor, thereby enabling the processor to read information, and write information to the storage medium. Of course, the storage media may also be an integral part of the processor.

The embodiments of the present disclosure further provides a computer program product, which may be directly loaded into the memory 803 and contains software codes, and the computer program may be loaded and executed by the computer to implement the method for correcting the collimator of radiotherapy equipment provided by the above embodiments.

Those skilled in the art should realize that in one or more examples described above, the functions described herein may be implemented in hardware, software, firmware, or any combinations thereof. In a case where implemented in software, the functions may be stored in the computer readable media or transmitted as one or more instructions or code on a computer readable media. Computer readable media comprise computer storage media and communication media, the communication media comprise any media that facilitates the transmission of computer programs from one place to another. The storage media may be any available media that may be accessed by a general purpose or special purpose computers.

In another embodiment, the embodiment of the present disclosure further provides a gamma knife apparatus. The structure of the gamma knife apparatus may be as shown in FIG. 3, including radiation sources, a collimator, a ray detector, and the apparatus for correcting the collimator of radiotherapy equipment as provided in the above embodiments. The ray detector is used to receive the rays passing through the collimation holes in the collimator and the isocenter plane of the radiotherapy equipment, generate a projection image of rays, and transmit the projection image of rays to the apparatus for correcting the collimator of the radiotherapy equipment.

The ray detector may be realized as the electronic field imaging device (EPID).

The specific embodiments described above further explain the objects, technical solutions and beneficial effects of the present disclosure. It should be understood that the above description is only the specific embodiments of the present disclosure, and is not intended to limit the scope of the present disclosure. Any modifications, equivalent substitutions, improvements and so on, made on the basis of the technical solutions of the present disclosure are intended to be comprised in the scope of the present disclosure.

What is claimed is:

1. A method of correcting a collimator of radiotherapy equipment, the method comprising:
   separately obtaining a projection image of rays sequentially passing through collimation holes in the collimator and an isocenter plane of the radiotherapy equipment in cases where the collimator moves to M positions, wherein the M positions include a design position of the collimator and at least one other position where a displacement difference from the design position is less than a preset distance, and the design position is a theoretical position of alignment of the collimator;
   determining a target position with a highest degree of alignment of the collimator from the M positions according to obtained projection images of rays; and
   recording position parameters corresponding to the target position, so as to control the collimator to move to the target position in a case where the radiotherapy equipment is used for treatment.

2. The method of correcting the collimator of the radiotherapy equipment according to claim 1, wherein determining the target position with the highest degree of alignment of the collimator from the M positions according to the projection images of rays, includes:
   determining the target position with the highest degree of alignment of the collimator from the M positions according to gray values and penumbra values of the projection images of rays.

3. The method of correcting the collimator of the radiotherapy equipment according to claim 2, wherein determining the target position with the highest degree of alignment of the collimator from the M positions according to gray values and penumbra values of the projection images of rays includes:
   generating isodose curves of a first percentage, isodose curves of a second percentage, and isodose curves of a third percentage of the rays according to the gray values and the penumbra values of the projection images of rays separately for the M positions to which the collimator moves, wherein the second percentage is a half of a sum of the first percentage and the third percentage; the isodose curves of the second percentage are isodose curves of 50%;
   calculating a similarity T between each isodose curve of the second percentage of the rays and a corresponding theoretical isodose curve of the second percentage separately for the M positions to which the collimator moves;
   calculating a distance L between each isodose curve of the first percentage and a corresponding isodose curve of the third percentage of the rays separately for the M positions to which the collimator moves; and
   determining the target position according to calculated similarities T and calculated distances L.

4. The method of correcting the collimator of the radiotherapy equipment according to claim 1, wherein determining the target position with the highest degree of alignment of the collimator from the M positions according to the projection images of rays, includes:
   generating isodose curves of a first percentage, isodose curves of a second percentage, and isodose curves of a third percentage of the rays according to the projection image of rays separately for the M positions to which the collimator moves, wherein the second percentage is a half of a sum of the first percentage and the third percentage; the isodose curves of the second percentage are isodose curves of 50%;
   calculating a similarity T between each isodose curve of the second percentage of the rays and a corresponding theoretical isodose curve of the second percentage separately for the M positions to which the collimator moves;
   calculating a distance L between each isodose curve of the first percentage and a corresponding isodose curve of the third percentage of the rays separately for the M positions to which the collimator moves; and
   determining the target position according to calculated similarities T and calculated distances L.

5. The method of correcting the collimator of the radiotherapy equipment according to claim 4, wherein generating the isodose curves of the first percentage, the isodose curves of the second percentage, and the isodose curves of the third percentage of the rays according to the projection image of rays separately for the M positions to which the collimator moves, includes:
   generating the isodose curves of the first percentage, the isodose curves of the second percentage, and the isodose curves of the third percentage of the rays according to gray values of the projection image of rays separately for the M positions to which the collimator moves.

6. The method of correcting the collimator of the radiotherapy equipment according to claim 4, wherein determining the target position according to the calculated similarities T and the calculated distances L, includes:
   calculating alignment parameters q of the collimation holes corresponding to the projection image of rays according to the similarities T and the distances L separately for the M positions to which the collimator moves;

calculating a total alignment parameter Q by taking a weighted average of the alignment parameters q of the collimation holes corresponding to the projection image of rays separately for the M positions to which the collimator moves; and determining a position at which the total alignment parameter Q is the largest among the M positions as the target position.

7. The method of correcting the collimator of the radiotherapy equipment according to claim 1, wherein the radiotherapy equipment includes radiation sources and the collimator, the collimator includes the collimation holes, and rays emitted from the radiation sources are focused to an isocenter of the radiotherapy equipment through the collimation holes.

8. A non-transitory computer storage medium, wherein the computer storage medium includes instructions that, when run on a computer, cause the computer to execute the method of correcting the collimator of the radiotherapy equipment according to claim 1.

9. A computer program product, wherein the computer program product comprises instructions that, when run on a computer, cause the computer to execute the method of correcting the collimator of the radiotherapy equipment according to claim 1.

10. An apparatus of correcting a collimator of radiotherapy equipment, the apparatus comprising:
a communication interface configured to receive projection images of rays each sequentially passing through collimation holes in the collimator and an isocenter plane of the radiotherapy equipment in cases where the collimator moves to M positions, wherein the M positions include a design position of the collimator and at least one other position where a displacement difference from the design position is less than a preset distance, and the design position is a theoretical position of alignment of the collimator; and
a processor connected to the communication interface, wherein the processor is configured to determine a target position with a highest degree of alignment of the collimator from the M positions according to obtained projection images of rays, and record position parameters corresponding to the target position.

11. The apparatus of correcting the collimator of the radiotherapy equipment according to claim 10, the apparatus further comprising:
a memory configured to store program codes and data of the apparatus of correcting the collimator of the radiotherapy equipment, and
a bus connected the processor to the memory via the bus.

12. The apparatus of correcting the collimator of the radiotherapy equipment according to claim 10, wherein the processor is configured to determine the target position with the highest degree of alignment of the collimator from the M positions according to gray values and penumbra values of the projection images of rays.

13. The apparatus of correcting the collimator of the radiotherapy equipment according to claim 10, wherein the processor is configured to:
generate isodose curves of a first percentage, isodose curves of a second percentage, and isodose curves of a third percentage of the rays according to the projection image of rays separately for the M positions to which the collimator moves, wherein the second percentage is a half of a sum of the first percentage and the third percentage; the isodose curves of the second percentage are isodose curves of 50%;
calculate a similarity T between each isodose curve of the second percentage of the rays and a corresponding theoretical isodose curve of the second percentage separately for the M positions to which the collimator moves;
calculate a distance L between each isodose curve of the first percentage and a corresponding isodose curve of the third percentage of the rays separately for the M positions to which the collimator moves; and
determine the target position according to calculated similarities T and calculated distances L.

14. The apparatus of correcting the collimator of the radiotherapy equipment according to claim 13, wherein the processor is configured to generate the isodose curves of the first percentage, the isodose curves of the second percentage, and the isodose curves of the third percentage of the rays according to gray values of the projection image of rays separately for the M positions to which the collimator moves.

15. The apparatus of correcting the collimator of the radiotherapy equipment according to claim 13, wherein the processor is configured to:
calculate alignment parameters q of the collimation holes corresponding to the projection image of rays according to the similarities T and the distances L separately for the M positions to which the collimator moves;
calculate a total alignment parameter Q by taking a weighted average of the alignment parameters q of the collimation holes corresponding to the projection image of rays separately for the M positions to which the collimator moves; and
determine a position at which the total alignment parameter Q is the largest among the M positions as the target position.

16. Radiotherapy equipment, comprising:
the apparatus of correcting the collimator of the radiotherapy equipment according to claim 10;
radiation sources; and
the collimator including the collimation holes, wherein the collimation holes are configured such that rays emitted from the radiation sources are focused to an isocenter of the radiotherapy equipment.

* * * * *